(12) United States Patent
Pietrantoni et al.

(10) Patent No.: US 8,045,156 B2
(45) Date of Patent: Oct. 25, 2011

(54) SYSTEM AND METHOD FOR CORRELATING PHOTORECEPTOR PIGMENTED FILM LAYER TO ELECTRICAL PERFORMANCE

(75) Inventors: Dante M. Pietrantoni, Rochester, NY (US); Kamran U. Zaman, Pittsford, NY (US); Jonathan H. Herko, Walworth, NY (US); Scott J. Griffin, Fairport, NY (US); Michael S. Roetker, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 148 days.

(21) Appl. No.: 12/490,183

(22) Filed: Jun. 23, 2009

(65) Prior Publication Data

US 2010/0321689 A1    Dec. 23, 2010

(51) Int. Cl.
*G01J 3/28* (2006.01)

(52) U.S. Cl. ......................................... 356/326

(58) Field of Classification Search .................. 356/326; 359/387
See application file for complete search history.

(56) References Cited

U.S. PATENT DOCUMENTS

| 5,784,162 A * | 7/1998 | Cabib et al. .................... 356/456 |
| 6,368,758 B1 * | 4/2002 | Camp et al. ...................... 430/12 |
| 2008/0097173 A1 * | 4/2008 | Soyemi et al. ................. 600/310 |

* cited by examiner

*Primary Examiner* — Tarifur Chowdhury
*Assistant Examiner* — Abdullahi Nur
(74) *Attorney, Agent, or Firm* — Pillsbury Winthrop Shaw Pittman LLP

(57) ABSTRACT

The presently disclosed embodiments are directed to a system and method for obtaining spectra of highly scattering pigmented layers and providing a spectral reflection ratio, which can be correlated to photoreceptor electrical performance. The present embodiments employ the use of dark field microscopy in combination with a noise reducing normalization technique to provide real-time production adjustments to optimize photoreceptor characteristics and/or performance.

21 Claims, 3 Drawing Sheets

SYSTEM AND METHOD FOR CORRELATING PHOTORECEPTOR PIGMENTED FILM LAYER TO ELECTRICAL PERFORMANCE

BACKGROUND

The presently disclosed embodiments relate generally to layers that are useful in imaging apparatus members and components, for use in electrostatographic, including digital, apparatuses. More particularly, the embodiments pertain to a system and method for providing measurements of photoreceptor layer thicknesses. The present embodiments employ the use of dark field microscopy in combination with a noise reducing normalization technique to provide representative spectral responses for highly scattering pigmented layers that are generally difficult to obtain with conventional methods and require more equipment. As it was discovered that such spectral measurements can be correlated to photoreceptor electrical characteristics, the present embodiments are also used to provide real-time production adjustments to optimize photoreceptor characteristics and/or performance.

An electrophotographic imaging member may be provided in a number of forms. For example, the imaging member may be a homogeneous layer of a single material such as vitreous selenium or it may be a composite layer containing a photoconductor and another material. In addition, the imaging member may be layered. These layers can be in any order, and sometimes can be combined in a single or mixed layer.

Multilayered photoreceptors or imaging members can have at least two layers, and may include a substrate, a conductive layer, an optional charge blocking layer (sometimes referred to as an "undercoat layer"), an optional adhesive layer, a photogenerating layer (sometimes referred to as a "charge generation layer," "charge generating layer," or "charge generator layer"), a charge transport layer, an optional overcoating layer and, in some belt embodiments, an anticurl backing layer. In the multilayer configuration, the active layers of the photoreceptor are the charge generation layer (CGL) and the charge transport layer (CTL). Enhancement of charge transport across these layers provides better photoreceptor performance. Overcoat layers are commonly included to increase mechanical wear and scratch resistance.

The term "photoreceptor" or "photoconductor" is generally used interchangeably with the terms "imaging member." The term "electrostatographic" includes "electrophotographic" and "xerographic." The terms "charge transport molecule" are generally used interchangeably with the terms "hole transport molecule."

The charge generation layer film is pigmented, and thus, conventional interference optics cannot be used to measure its thickness because a clear or translucent film would be needed to provide the required interference fringes. In addition, contact measurement devices do not provide the resolution needed to measure these sub-micron thick films. Because of this "gap" in measurement technology, current manufacturing processes of photoreceptor layers may result in inconsistent product performance. For example, some photoreceptors can exhibit high $V_{low}$, reduced photosensitivity, and print defects. It was observed that these abnormal parameters can be correlated to the spectral reflection ratio of the films representative spectra. Conventional methods, however, require the coating of a full device, determining or checking the $V_{low}$ of the device, and subsequently feeding of the information back to the production line. As used herein, $V_{low}$ refers to the surface voltages of photoreceptor after light exposure, and "photosensitivity" refers to the surface voltage change rate to the exposure energy.

Thus, new and effective means to provide accurate and fast measurement of photoreceptor layers, especially those layers that are pigmented, are important to future enhancement of photoreceptor production and overall xerographic performance. In this regard, a measurement system that can provide real-time measurement and feedback of critical xerographic control parameters or variables during production will be highly desirable.

SUMMARY

According to aspects illustrated herein, there is provided a system for providing correlates of imaging member layer relative thickness, comprising: a reflected light microscope, comprising a light source and a dark field objective for applying a light beam to a pigmented imaging layer, wherein a reflected beam is produced; a beam splitter and fiber optic cable for transporting the reflected beam to a spectrometer; a spectrometer for obtaining a spectrum of the pigmented imaging layer positioned on a top portion of an imaging member and defining the spectrum associated with the pigmented imaging layer, wherein the spectrum is normalized such that a base spectrum is subtracted from a composite spectrum of the imaging member to define the spectral response associated with the topmost pigmented imaging layer; and circuitry for correlating imaging member characteristics with the measurements obtained from the spectrometer and microscope, wherein such correlating information is used to adjust imaging layer production or monitor imaging layer wear.

In another embodiment, there is provided a method for providing measurement of imaging member relative layer thickness, comprising: measuring a spectra value of a pigmented imaging layer positioned on a top portion of a multi-layer imaging member, wherein the spectra value is normalized such that a base spectra value is subtracted from an overall spectra value of the multi-layer imaging member to define the spectra value associated with the pigmented imaging layer; measuring the pigmented imaging layer to determine pigment spectral characteristic of pigment deposited in the pigmented imaging layer; correlating imaging member characteristics with the measurements obtained, wherein such correlating information is used to determine the measurements that produce optimal imaging member electrical characteristics; and using the correlating information to adjust imaging layer production or monitor imaging layer wear.

Yet another embodiment, there is provided a method for providing measurement and adjustment of imaging member relative layer thickness, comprising: measuring a spectra value of a pigmented imaging layer positioned on a top portion of an imaging member, wherein the spectra value is normalized such that a base spectra value is subtracted from an overall spectra value of the imaging member to define the spectra value associated with the pigmented imaging layer; measuring the pigmented imaging layer to determine pigment spectral characteristic of pigment deposited in the pigmented imaging layer; correlating imaging member characteristics with the measurements obtained, wherein such correlating information is used to determine the measurements that produce optimal imaging member characteristics; and using the correlating information to adjust imaging layer production or monitor imaging layer wear, wherein algorithms based on smoothing and absorbance ratios calculated from the measurements obtained are used for correlating the imaging member characteristics with the measurements.

BRIEF DESCRIPTION OF THE DRAWINGS

For a better understanding, reference may be had to the accompanying figure.

Unless otherwise noted, the same reference numeral in different Figures refers to the same or similar feature.

DETAILED DESCRIPTION

Figure 1:
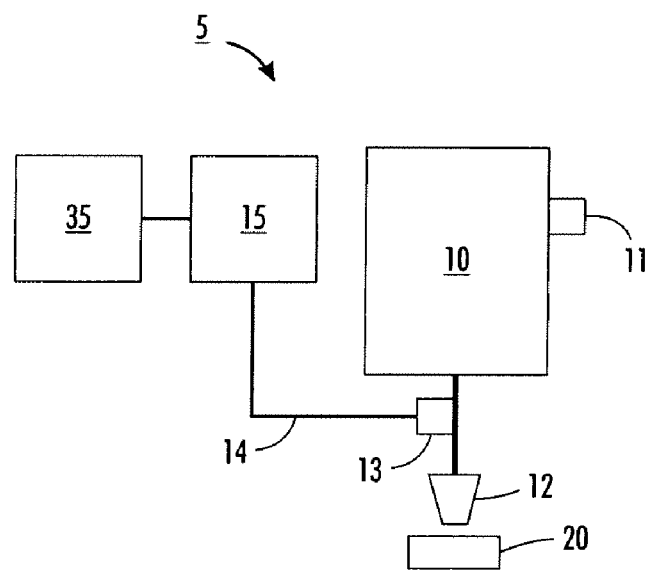
FIG. 1 a schematic of a system for providing measurements of photoreceptor layer thickness and real-time production adjustments in accordance with the present embodiments.

In the following description, reference is made to the accompanying drawings, which form a part hereof and which illustrate several embodiments. It is understood that other embodiments may be utilized and structural and operational changes may be made without departure from the scope of the present disclosure. The same reference numerals are used to identify the same structure in different figures unless specified otherwise. The structures in the figures are not drawn according to their relative proportions and the drawings should not be interpreted as limiting the disclosure in size, relative size, or location.

Representative electrophotographic photoreceptors or imaging members may be generally provided with an anticurl layer, a supporting substrate, an electrically conductive ground plane, an undercoat layer, an adhesive layer, a charge generating layer, a charge transport layer, an overcoating layer, and a ground strip. In embodiments, the imaging layer, containing both charge generating material and charge transport material, takes the place of separate charge generating layer and charge transport layer.

In fabricating a photoreceptor, a charge generating material (CGM) and a charge transport material (CTM) may be deposited onto the substrate surface either in a laminate type configuration where the CGM and CTM are in different layers or in a single layer configuration where the CGM and CTM are in the same layer along with a binder resin. The photoreceptors can be prepared by applying over the electrically conductive layer the charge generation layer and, optionally, a charge transport layer. In embodiments, the charge generation layer and, when present, the charge transport layer, may be applied in either order.

The presently disclosed embodiments relate generally to a system and method for providing representative spectral responses for highly scattering pigmented layers. The present embodiments employ the use of dark field microscopy in combination with a noise reducing normalization technique via a spectrometer to give a spectral reflection ratio of pigmented and highly scattering films from representative spectra. The charge generating film is pigmented, and thus, conventional interference optics cannot be used to measure its thickness because a clear or translucent film would be needed. In addition, contact measurement devices don't provide the resolution needed to measure these sub-micron films.

Thus, the present embodiments provide a method for providing a spectral reflection ratio, which when correlated to electrical performance, would lead to adjustment of imaging member layer thickness. This spectral reflection ration is obtained from a high S/N spectrum, made possible by the use of dark field optics (oblique illumination) and including a noise-reducing normalization technique. The method comprises obtaining the spectrum of a pigmented imaging layer, via a spectrometer, wherein the spectrum value is normalized such that a base spectrum of the layers underlying the top layer(s) of interest is subtracted from the Spectrum of the overall imaging device (e.g., all layers) to obtain a resulting spectrum for the top imaging layer(s) of interest. In a particular embodiment, the spectra of a multi layer device, without the top layer of interest is obtained as the base spectrum (or reference scan). A device, including the top layer of interest, is also measured (test scan). The spectrum of the reference scan is subtracted from that of the test scan to obtain the spectrum of the top layer of interest. This noise-reducing normalization method is based on the subtraction of the reference spectrum and the use of oblique illumination, via dark field optics to isolate the top most layers spectral response. In embodiments, the pigmented imaging layer can be the charge generation layer, or any other non-transparent granular film that scatters light, such as for example, undercoat layers, charge transport layers, overcoat layers, and the like. The method further comprises correlating photoreceptor characteristics with the measurements obtained, wherein such correlating information is used to determine the measurements that produce optimal photoreceptor electrical characteristics. The correlating information can then be subsequently used to adjust imaging layer production or monitoring imaging layer wear. The correlating information can be pigmented imaging layer thickness, pigment optical density, $V_{low}$, and the like. In specific embodiments, the spectral reflection ratio is obtained from a reflected light microscope, equipped with dark field optics, a beam splitter and spectrometer. In further embodiments, the method comprises storing the normalization and correlation data in memory.

In the present embodiments, the spectrum is normalized such that a base spectrum is subtracted from the spectrum of the imaging layer of interest. In addition, the method may employ algorithms based on smoothing and integration time, spectrometer spectral range, and the like, to further increase the spectral S/N. % reflectance ratios calculated from the spectrum can be correlated to pigment concentrations and photoreceptor electrical characteristics. In particular embodiments, the following algorithm is used for correlating the photoreceptor electrical characteristics with the measurements obtained: % Reflectance at a reference λ/% Reflectance at peak λ.

The present embodiments provide a method and system for providing representative spectral responses for highly pigmented or opaque layers, such as the charge generation layer, but also integrating such method into a system that can provide fast, real-time measurements (spectral reflection Ratio). As it was discovered that such measurements can be correlated to photoreceptor characteristics, the present embodiments are also used to provide real-time production adjustments to optimize photoreceptor characteristics and parameters, such as layer thickness, and enhance overall photoreceptor production and performance. The method and system can be used as part of imaging member production to optimize production parameters and imaging member characteristics as well as being integrated into an operating image forming apparatus to test for imaging member characteristics, such as for example, the degree of photoreceptor wear.

In particular embodiments, the system 5 comprises a microscope 10, and more particularly in a specific embodiment, a reflected light microscope, and spectrometer 15. In embodiments, the spectrometer is a UV/Vis spectrometer. In the present embodiments, the system is intended to include any type of optical spectrometer or optical detector that may be used for obtaining the pigments spectral characteristic. As seen in FIG. 1, the system 5 employs a spectrometer 15 that provides a compound signal measured from the tested photoreceptor layer 20. The compound signal comprises the full spectral information of the entire imaging device and all its layers. For example, the compound signal can include the spectra values of an aluminum substrate and all films deposited upon the substrate to form the imaging device. The system has an optical assembly comprising a light source 11, in optical alignment with a microscope. When a test sample 20 is positioned under the objective 12, the light source 11 directs a light beam through the microscope optics to the test sample 20 so that at least a portion of the scattered light is reflected back through the objective 12 and the beam directed by the beam splitter 13 and fiber optic cable 14 to the spectrometer 15, defining of the spectral characteristic associated with the test sample 20. The system 5 is designed to convert the actual value to a normalized value by appropriate circuitry 35 in communication with the system 5 such that the normalized value obtained by the spectrometer 15 gives the characteristic data of the top most pigmented layer. The circuitry 35 comprises both system hardware and software, which operate in combination to perform the necessary calculations to obtain the desired measurements, such as for example, pigment spectral reflection ratios. A normalization factor is obtained by determining the characteristic data, such as the base spectrum of the layers underlying the top most pigmented layer of interest and using that value to subtract from the spectrum of the compound signal obtained from the multi-film imaging device in order to isolate the characteristic data of the top most pigmented layer. The circuitry software implements the subtraction of the base spectra value from that of the test scan and provides the measurements for the spectra of the top layer of interest. The normalization factor may be stored in system memory 36. In further embodiments, the circuitry is remotely located from the system comprising the microscope and spectrometer and the data from the microscope and spectrometer is collected and sent to the circuitry for calculating the measurements.

To evaluate the S/N of representative spectra using this technique, the S/N ratios for each spectrum were approximated using the standard error of the second order polynomial used to fit the data obtained. This was a reliable standard to use as a measure of signal to noise, as it represents the difference between the data to the model. As a system, further enhancement to S/N would be made through algorithms for smoothing based on moving averages, adjusting integration time, wavelength range, and the like, and would then be applied by the system circuitry 35 to enable correlating the spectral response of the top most pigmented layer with various parameters and distinguish varying rates of deposited dry pigment, electrical performance, and the like, which can be used in a feedback loop to optimize photoreceptor layer production.

Figure 2:
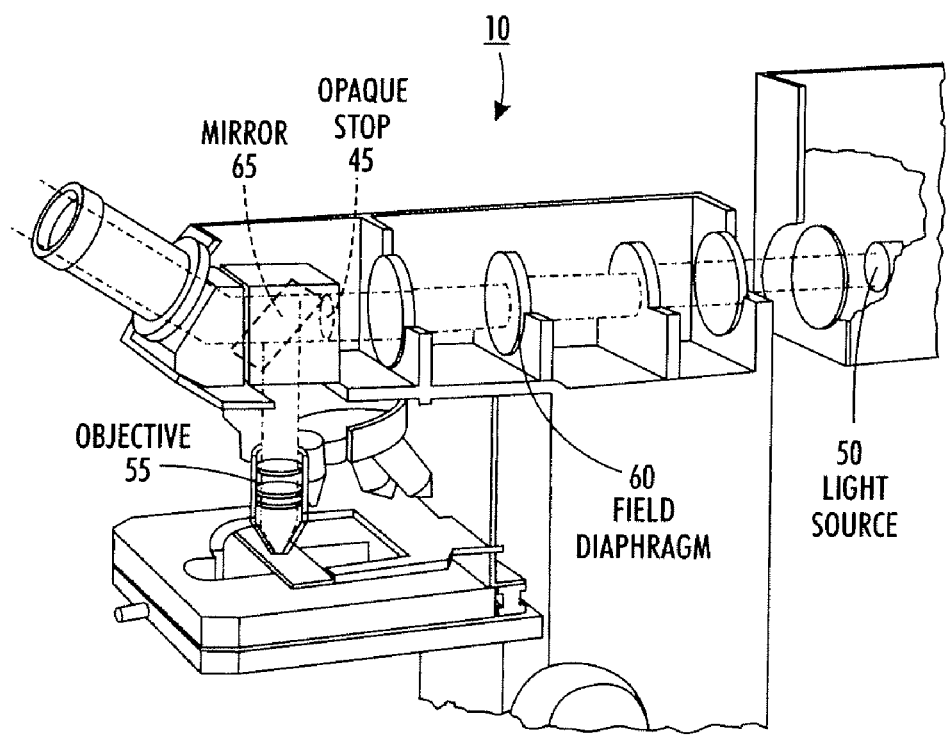
FIG. 2 represents a diagram of a reflected light microscope used as part of the system in accordance with the present embodiments.

As discussed, the system 5 further comprises a reflected light microscope 10 to provide further details of high S/N characteristics of the top most pigmented layer. One of the most effective ways to improve contrast in the reflected light microscope is to utilize darkfield illumination. Thus, in particular embodiments, as shown in FIG. 2, the reflected light microscope 10 is used with a dark field configuration in which the microscope 10 is set up with a contrasting dark field slide 45 (e.g., an opaque stop) and dark field ready objective 55. In reflected darkfield microscopy, the opaque stop is placed in the path of the light (from the light source 50) traveling through the vertical illuminator 60 so that only the peripheral rays of light reach the deflecting mirror 65. These rays are reflected by the mirror 65 and pass through a hollow collar surrounding the objective 55 to illuminate the specimen at highly oblique angles.

The dark field technique and corresponding dark field ready objective provides the highly oblique illumination needed to enhance the contrast of the top most pigmented surface. This oblique and diffused illumination ensures the capture of surface boundaries and other features that cannot be detected with specular reflection. Thus, the system of the present embodiments uses such measurement data and correlations obtained from both the spectrometer and microscope to subsequently determine what adjustments are necessary during production to optimize the characteristics of the resulting photoreceptor layers. For example, the system and method described herein can provide a spectral absorption ratio for the imaging device and its layers and this absorbance ratio value can be paired to a $V_{low}$ value such that a range of the ratio values can be established as being correlated to desirable $V_{low}$ values. The absorbance ratio is a ratio of the absorbance at a reference wavelength divided by the absorbance at a peak wavelength.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Example 1

Figure 3:
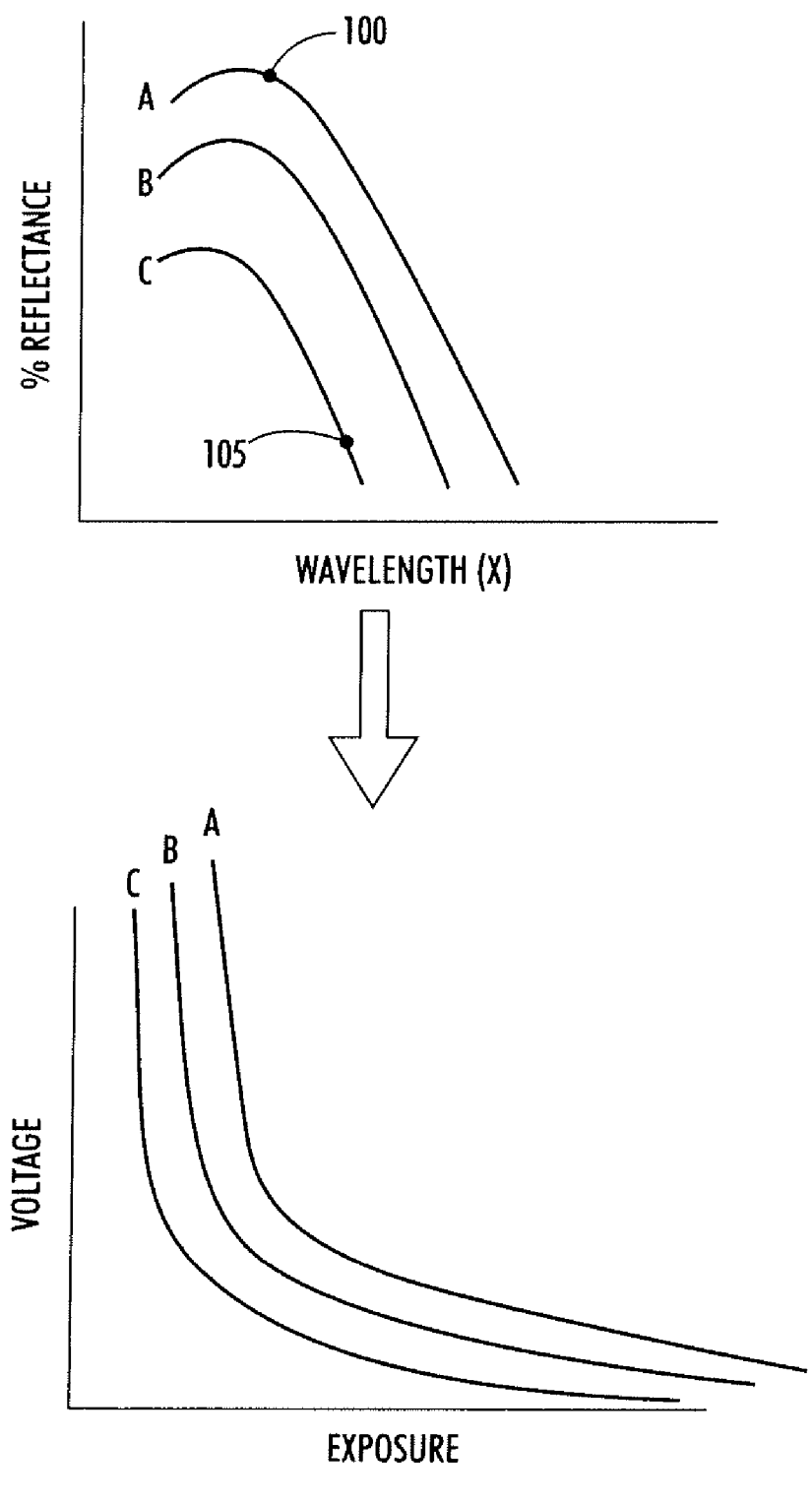
FIG. 3 represents a graph illustrating correlation of photoreceptor layer thickness with reflectance of the layer material in accordance with the present embodiments.

In experimental trials, it was shown that the percentage of reflectance as a function of wavelength used could be used as a correlate to thickness of pigmented photoreceptor layers. As seen in FIG. 3, photoreceptor layer thickness can be correlated with reflectance of the layer material. Namely, a higher % reflectance curve 100 comes from a "thinner" or less optically dense material. The lowest % reflectance curve 105 comes from the "thicker" or more optically dense layer coatings. In addition, the thinner or thicker layers can be further correlated with electrical parameters such as $V_{low}$.

Example 2

Figure 4:
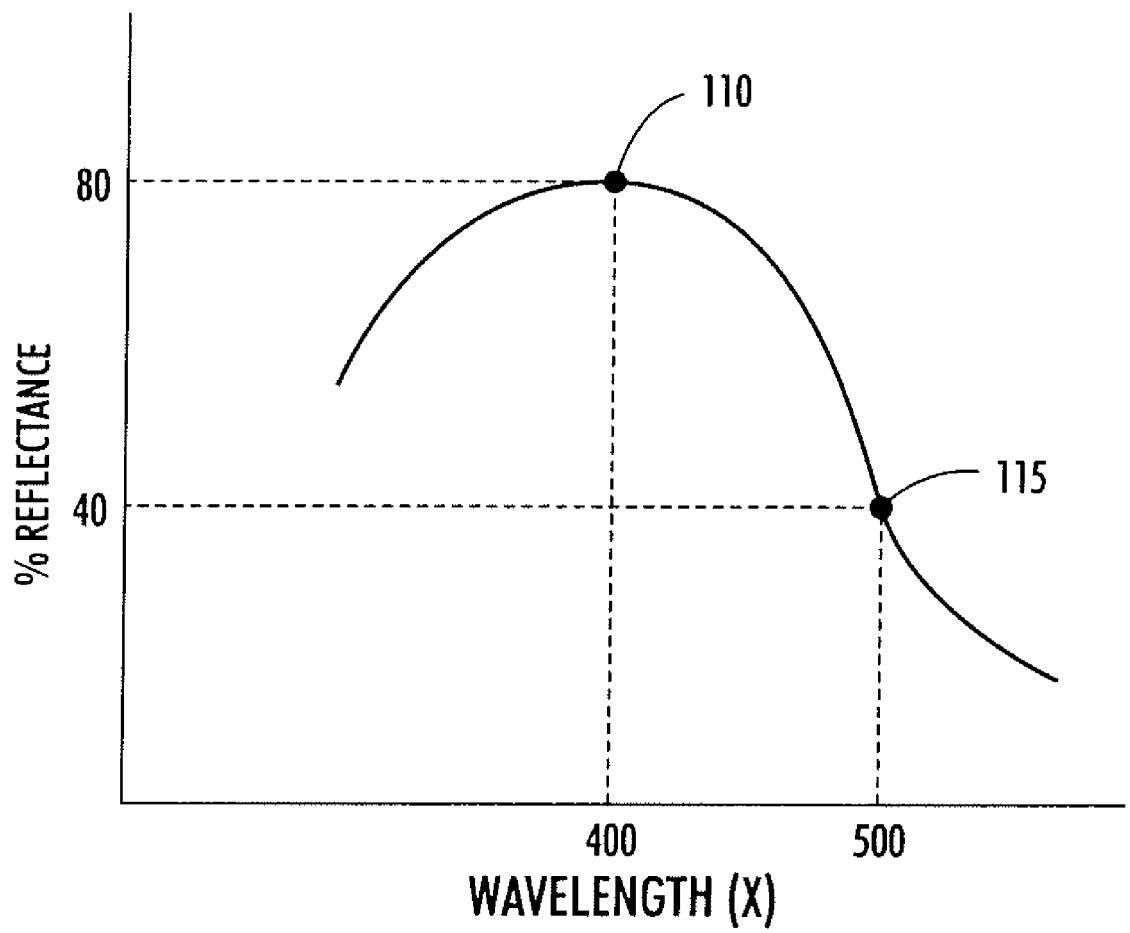
FIG. 4 represents a graph illustrating calculation of a spectral reflection ratio of pigmented and highly scattering films from representative spectra in accordance with the present embodiments.

In FIG. 4, it is demonstrated that a calculation of a spectral reflection ratio of pigmented and highly scattering films can be obtained from representative spectra of the photoreceptor layers. As illustrated, the spectral reflection ratio is obtained from data points indicating a peak reflectance value 110 and a reference reflectance value 115 taken from the graph. Namely, the spectral reference ratio would be obtained by calculating a ratio of the reference reflectance value 115 to the peak reflectance value 110. As illustrated in FIG. 4, the spectral reference ratio would be 40/80 or 0.5.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A system for providing correlates of a xerographic imaging member layer relative thickness, comprising:
    a reflected light microscope, comprising a light source and a dark field objective for applying a light beam to a pigmented xerographic imaging layer, wherein a reflected beam is produced;
    a beam splitter and fiber optic cable for transporting the reflected beam to a spectrometer;
    a spectrometer for obtaining a spectrum of the pigmented xerographic imaging layer positioned on a top portion of a xerographic imaging member and defining the spectrum associated with the pigmented xerographic imaging layer, wherein the spectrum is normalized such that a base spectrum is subtracted from a composite spectrum of the xerographic imaging member to define the spectral response associated with the topmost pigmented xerographic imaging layer; and
    circuitry for correlating imaging member characteristics with the measurements obtained from the spectrometer and microscope, wherein such correlating information is used to adjust xerographic imaging layer production or monitor xerographic imaging layer wear.

2. The system of claim 1, wherein the microscope is a reflected light microscope.

3. The system of claim 1, wherein the correlated xerographic imaging member characteristics are selected from the group consisting of pigmented xerographic imaging layer thickness, pigment optical density in the xerographic imaging layer, $V_{low}$, and mixtures thereof.

4. The system of claim 1, wherein the system further comprises a memory for storing normalization and correlation data.

5. The system of claim 1, wherein the microscope is used in a dark field configuration.

6. The system of claim 5, wherein the microscope includes a contrasting dark field slide and dark field ready objective.

7. The system of claim 1, wherein the pigmented xerographic imaging layer is selected from the group consisting of a charge generation layer, a charge transport layer, an undercoat layer, and an overcoat layer.

8. A method for providing measurement of xerographic imaging member relative layer thickness, comprising:
    measuring a spectra value of a pigmented xerographic imaging layer positioned on a top portion of a multi-layer xerographic imaging member, wherein the spectra value is normalized such that a base spectra value is subtracted from an overall spectra value of the multi-layer xerographic imaging member to define the spectra value associated with the pigmented xerographic imaging layer;
    measuring the pigmented xerographic imaging layer to determine pigment spectral characteristic of pigment deposited in the pigmented xerographic imaging layer;
    correlating xerographic imaging member characteristics with the measurements obtained, wherein such correlating information is used to determine the measurements that produce optimal xerographic imaging member electrical characteristics; and
    using the correlating information to adjust xerographic imaging layer production or monitor xerographic imaging layer wear.

9. The method of claim 8, wherein the spectra value is measured by a spectrometer.

10. The method of claim 8, wherein the pigment spectral characteristic of pigment in the xerographic imaging layer is measured by a microscope.

11. The method of claim 10, wherein the microscope is a reflected light microscope and is used in a dark field configuration and the reflected light microscope further includes a contrasting dark field slide and dark field ready objective.

12. The method of claim 8, wherein the correlated xerographic imaging member characteristics are selected from the group consisting of pigmented imaging layer thickness, pigment optical density in the xerographic imaging layer, $V_{low}$, and mixtures thereof.

13. The method of claim 8 further comprising storing the normalization and correlation data in memory.

14. The method of claim 8, wherein the pigmented xerographic imaging layer is selected from the group consisting of a charge generation layer, a charge transport layer, an undercoat layer, and an overcoat layer.

15. A method for providing measurement and adjustment of xerographic imaging member relative layer thickness, comprising:
    measuring a spectra value of a pigmented xerographic imaging layer positioned on a top portion of a xerographic imaging member, wherein the spectra value is normalized such that a base spectra value is subtracted from an overall spectra value of the xerographic imaging member to define the spectra value associated with the pigmented xerographic imaging layer;
    measuring the pigmented xerographic imaging layer to determine pigment spectral characteristic of pigment deposited in the pigmented xerographic imaging layer;
    correlating xerographic imaging member characteristics with the measurements obtained, wherein such correlating information is used to determine the measurements that produce optimal xerographic imaging member characteristics; and
    using the correlating information to adjust xerographic imaging layer production or monitor xerographic imaging layer wear, wherein algorithms based on smoothing and absorbance ratios calculated from the measurements obtained are used for correlating the xerographic imaging member characteristics with the measurements.

16. The method of claim 15, wherein the spectra value is measured by a spectrometer.

17. The method of claim 15, wherein the pigment spectral characteristic of pigment in the xerographic imaging layer is measured by a microscope.

18. The method of claim 15, wherein the following algorithm is used for correlating the xerographic imaging member characteristics with the measurements obtained: % Reflectance at a reference $\lambda$/% Reflectance at peak $\lambda$.

19. The method of claim 15, wherein the correlated xerographic imaging member characteristics are selected from the group consisting of pigmented imaging layer thickness, pigment optical density in the xerographic imaging layer, $V_{low}$, and mixtures thereof.

20. The method of claim 15 further comprising storing the normalization and correlation data in memory.

21. The method of claim 15, wherein the pigmented xerographic imaging layer is selected from the group consisting of a charge generation layer, a charge transport layer, an undercoat layer, and an overcoat layer.

* * * * *